United States Patent
Klug et al.

(10) Patent No.: US 6,326,514 B1
(45) Date of Patent: Dec. 4, 2001

(54) PROCESS FOR THE PREPARATION OF ETHER CARBOXYLIC ACIDS WITH LOW RESIDUAL ALCOHOL CONTENT

(75) Inventors: Peter Klug, Grossostheim; Rainer Kupfer, Hattersheim; Ignaz Wimmer, Winhöring; Rüdiger Winter, Frankfurt, all of (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 09/596,418

(22) Filed: Jun. 19, 2000

(30) Foreign Application Priority Data

Jun. 19, 1999 (DE) ............................................. 199 28 128

(51) Int. Cl.$^7$ ..................... C07C 59/125; C07C 59/305; C07C 59/58
(52) U.S. Cl. ........................... 562/583; 562/588; 568/620
(58) Field of Search .................... 562/583, 588; 554/124; 568/620

(56) References Cited

U.S. PATENT DOCUMENTS

| | | |
|---|---|---|
| 4,223,163 | 9/1980 | Guilloty . |
| 4,239,917 | 12/1980 | Yang . |
| 4,894,485 | 1/1990 | Behler et al. . |
| 5,001,245 * | 3/1991 | Nakano et al. . |
| 5,233,087 * | 8/1993 | Cripe . |
| 5,420,315 * | 5/1995 | Uhrig et al. . |
| 5,523,479 * | 6/1996 | Sanders et al. . |

FOREIGN PATENT DOCUMENTS

| | | |
|---|---|---|
| 0 166 958 | 1/1986 | (EP) . |
| 0 295-578 | 12/1988 | (EP) . |

OTHER PUBLICATIONS

EPO Search Report.
Derwent Patent Family Abstract for EP 0 166 958.

* cited by examiner

*Primary Examiner*—Johann Richter
*Assistant Examiner*—Sikarl A. Winterspoon
(74) *Attorney, Agent, or Firm*—Susan S. Jackson; Scott E. Hanf

(57) ABSTRACT

The invention provides a process for the preparation of ether carboxylic acids or alkali metal or ammonium salts thereof with low residual alcohol content, which comprises firstly converting a mono- or polyhydric alcohol into the corresponding alkoxide using a substoichiometric amount between 5 and 95 mol % of a basic compound, and then reacting the alkoxide with alkylene oxides, and, if necessary after distilling off the residual alcohol which remains, alkylating the highly alkaline reaction mixture, which comprises more than 5 mol % of alkoxylated alkoxides, directly with a chloroacetic acid derivative, and, if necessary, converting the alkylated product into the free ether carboxylic acid by acidification with mineral acid.

5 Claims, No Drawings

PROCESS FOR THE PREPARATION OF ETHER CARBOXYLIC ACIDS WITH LOW RESIDUAL ALCOHOL CONTENT

BACKGROUND OF THE INVENTION

The present invention relates to a new type of process for the preparation of ether carboxylic acids with low residual alcohol content.

Ether carboxylic acids, i.e. organic carboxylic acids which, in addition to the carboxyl function, carry one or more ether bridges, or alkali metal or amine salts thereof, are known as mild detergents with high lime soap dispersibility. They are used both in detergent and cosmetic formulations, and also in industrial applications (e.g. metal working fluids, cooling lubricants). According to the prior art, these products are prepared either by alkylation of alcohol or fatty alcohol ethoxylates or propoxylates with chloroacetic acid derivatives (Williamson ether synthesis) or from the same starting materials by oxidation with various reagents (atmospheric oxygen, hypochlorite, chlorite) with catalysis with various catalysts. The disadvantage of the Williamson synthesis is the incomplete conversion of the parent ethoxylate to the ether carboxylic acid or salt thereof. Despite excesses of chloroacetic acid derivative, the conversions are often only between 70 and 85%. Residual amounts of ethoxylate or of the fatty alcohol on which the ethoxylate is based remain in the end-product since the former reacts more slowly with chloroacetic acid or the sodium salt of chloroacetic acid than an ethoxylated alcohol. This is particularly unfavorable when alcohols having low degrees of ethoxylation are used as base material. These ethoxylates can comprise between 5 and 30% of residual fatty alcohol. Since the fatty alcohol has lower reactivity in the Williamson synthesis than an ethoxylated fatty alcohol, this likewise leads to a high residual fatty alcohol content in the ether carboxylic acid and also to poorer conversions to the ether carboxylic acid. For this reason, using ethoxylates of lower fatty alcohol having chain lengths of $C_5$–$C_{12}$ in the process often leads to odor problems as a result of the residual alcohol content since these fatty alcohols are odor-intensive.

SUMMARY OF THE INVENTION

There is therefore a need for processes which reduce the residual alcohol content in the ether carboxylic acid. This can be achieved, for example, by using classical narrow-range catalysts during the ethoxylation; these lower the residual content of fatty alcohol in the ethoxylate and therefore also the fatty alcohol content in the ether carboxylic acid. However, the catalyst used, as disclosed, for example, in EP-A-0 295 578, is often salts of various carboxylic acids containing polyvalent ions (e.g. calcium), which have to be separated off again or cause problems as a result of clouding. In addition, this catalyst has to be prepared in an upstream reaction stage.

Surprisingly, we have now found that this problem can be circumvented in a simple manner if fatty alcohols are firstly reacted with alkylene oxides using noncatalytic amounts of alkali metal catalyst (NaOH, KOH, alkoxides greater than 5 mol %), and the resulting highly alkaline reaction mixtures, which consist of a mixture of ethoxylated alcohols and alkoxides of various polyalkylene glycol ethers, are then converted into the corresponding ether carboxylic acid in a classic Williamson synthesis using sodium chloroacetate. This leads to a significant reduction in the residual content of fatty alcohol in the ether carboxylic acid without special catalysts, which, inter alia, also leads to products with improved odor. Additionally, a narrow-range distribution of the resulting ether carboxylic acid is obtained, which can lead to advantageous property profiles (e.g. better solubility).

DESCRIPTION OF THE PREFERRED EMBODIMENTS

The invention provides a process for the preparation of ether carboxylic acids or alkali metal or ammonium salts thereof with low residual alcohol content, which comprises firstly converting a mono- or polyhydric alcohol into the corresponding alkoxide using a substoichiometric amount between 5 and 95 mol % of a basic compound, and then reacting the alkoxide with alkylene oxides, and, if necessary after distilling off the residual alcohol which remains, alkylating the highly alkaline reaction mixture, which comprises more than 5 mol % of alkoxylated alkoxides, directly with a chloroacetic acid derivative, and, if necessary, converting the alkylated product into the free ether carboxylic acid by acidification with mineral acid.

Suitable base fatty alcohols for the process described here are linear or branched, saturated or unsaturated alcohols having from 1 to 30 carbon atoms, for example fatty alcohols having 1–30 carbon atoms, and alkylphenols having a $C_1$–$C_{20}$-alkyl radical. Preference is given to $C_6$–$C_{22}$-fatty alcohols. The above alcohols are reacted in the process according to the invention with alkylene oxides, e.g. ethylene oxide, propylene oxide, butylene oxide or mixtures of various such alkylene oxides, preference being given to ethylene oxide or mixtures of ethylene oxide and propylene oxide. Based on fatty alcohol, 1–30 mol of alkylene oxide are admitted, preferably 1–12 mol.

Basic compounds which can be used for the preparation of the ethoxylated alkoxides are alkaline earth metal/alkali metal hydroxides or alkoxides (sodium methoxide, sodium ethoxide, potassium tert-butoxide), preference, however, being given to alkali metal hydroxides, particularly sodium hydroxide or potassium hydroxide.

The basic compounds are used in amounts of about 5–95 mol %, based on the mono-or polyhydric alcohol, preferably between 15 and 90 mol %, particularly preferably between 20 and 60 mol %.

Starting from the base alcohol, the alkoxides required for the alkoxylation are prepared by reaction with the basic compounds. In order to avoid higher proportions of byproducts (glycols, glycol ethers of lower alcohols) in the end-product, the water of reaction which forms in the process or the corresponding lower alcohol must be removed from the reaction mixture prior to reaction with the alkylene oxide. This can be achieved either by reacting the alcohol with an alkali metal hydroxide and distilling off the water of reaction, or by reacting the base alcohol with an alkoxide of a lower alcohol and distilling off the lower alcohol. In the former case, the fatty alcohol can also serve as water entrainer for the water of reaction.

The resulting mixture of fatty alcohol and the corresponding alkoxide is then reacted with about 1–30 mol of an alkylene oxide, preferably ethylene oxide and/or propylene oxide, the reaction temperatures during the process being about 80–160° C. Here, compared with a reaction catalyzed with small amounts of alkali, the homolog distribution is narrower, which leads to a reduction in the amount of residual alcohol. If necessary, more of the residual alcohol which still remains can be distilled off under reduced pressure.

In the subsequent reaction step, the alkoxide/alcohol ethoxide mixture is reacted with a chloroacetic acid derivative and a base, preferably the dry sodium salt of chloroacetic acid and sodium hydroxide. This can be achieved by reacting the ethoxylate/alkoxide mixture with 100–150 mol % of sodium chloroacetate at 30–100° C. and simultaneously or subsequently adding solid sodium hydroxide or potassium hydroxide such that the sum of the base already present in the ethoxylate/alkoxide mixture and of the amount of base additionally added corresponds to the amount of sodium chloroacetate. The amount of base already present from the reaction with the alkylene oxide can thus be utilized directly for the subsequent Williamson synthesis and must not, as is the case for the synthesis of a standard ethoxylate, be washed out.

Following the alkylation reaction, the resulting solution of the ether carboxylic acid alkali metal salt can either be used directly as detergent or be converted into the free ether carboxylic acid to reduce the salt content. For this purpose, strong mineral acid (hydrochloric acid, sulfuric acid) is used to acidify the mixture to pH<3, and the ether carboxylic acid is separated off hot as upper phase by phase separation above its cloud point.

As the following experimental examples show, the process illustrated here can be used to obtain ether carboxylic acids or ether carboxylic acid salts having narrower homolog distribution and higher conversions and lower residual alcohol contents.

EXAMPLES

Example 1

Isononyl Alcohol +3 EO Ether Carboxylic Acid

A 4 l stirred apparatus fitted with water separator is charged with 2163 g (15.0 mol) of isononyl alcohol and 150 g (3.75 mol) of sodium hydroxide under nitrogen and the reaction mixture is heated to 150° C. A vacuum is then slowly applied until the mixture is boiling and regulated such that the boiling temperature is always 150° C., a total of 62.3 g (3.46 mol) of water being removed azeotropically. Boiling begins at about 600 mbar. The final vacuum is about 180 mbar, is achieved after about 1 h and is then maintained for about 2 h.

2252 g (15.0 mol) of the above isononyl alcohol/isononyl alkoxide mixture are charged to a 5 l ethoxylation apparatus under 1 bar of nitrogen and heated to 160° C. 1982 g (45.0 mol) of ethylene oxide are then metered in over about 1.5 h at 160° C., post-reaction for 1 h at 160° C. until the pressure is constant. The remaining isononyl alcohol which is present is distilled off at a reboiler temperature of 125° C. and a reduced pressure of 25 mbar (total 462 g).

1886 g (5.9 mol) of the above isononyl alcohol/isononyl alkoxide ethoxylate distillation residue are charged to a 10 l stirred apparatus under nitrogen and heated to 40° C. 825 g (7.10 mol) of sodium chloroacetate are then introduced and the reaction mixture is subsequently heated to 50° C. After 45 min in each case, 208 g (5.20 mol) of NaOH microprills are introduced in three equal portions at 50° C. Post-reaction 45 min at 50° C. and 2 h at 70° C. 3259 g (7.15 mol) of 8% hydrochloric acid are then run in, and the mixture is heated to 95° C. and transferred to a 10 l stirred apparatus with bottom discharge. Phase separation takes place after 15 min at 95° C., about 3816 g of aqueous lower phase being separated off. 2391 g of isononyl alcohol +3 EO ether carboxylic acid are obtained.

TABLE 1

EO Homolog distribution before the alkylation step

|  | Standard ethoxylation (1 mol % of NaOH) | Example 1 (25 mol % of NaOH) |
|---|---|---|
| Degree of ethoxylation | 3.0 | 3.9(3.0*) |
| Isononyl alcohol (area %) | 22.0 | 0.6(9.0*) |
| Isononyl alcohol + 1 EO (area %) | 12.0 | 9.9 |
| Isononyl alcohol + 2 EO (area %) | 11.9 | 15.4 |
| Isononyl alcohol + 3 EO (area %) | 10.9 | 17.6 |
| Isononyl alcohol + 4 EO (area %) | 9.2 | 17.1 |
| Isononyl alcohol + 5 EO (area %) | 7.3 | 14.2 |
| Isononyl alcohol + 6 EO (area %) | 6.2 | 10.5 |
| Isononyl alcohol + 7 EO (area %) | 5.2 | 7.0 |
| Isononyl alcohol + 8 EO (area %) | 4.2 | 4.1 |
| Isononyl alcohol + 9 EO (area %) | 3.4 | 2.2 |
| Isononyl alcohol + 10 EO (area %) | 2.6 | 1.0 |
| Isononyl alcohol + 11 EO (area %) | 1.8 | 0.2 |
| Total area % | 96.7 | 100.0 |
| Isononyl alcohol (% by weight) | about 17 | 0.5 |

*before the distillation step; because of the distilled-off residual alcohol, the average degree of ethoxylation shifts to higher values.

Characteristics of the ether carboxylic acid

|  | Acid number (mg KOH/g) | Content according to acid number (%) | Catalyst/ amount |
|---|---|---|---|
| Ether carboxylic acid based on standard ethoxylate | 126.0 (3.0 EO) | 76.4 | NaOMe 1.0 mol % |
| Example 1 | 130.6 (3.9 EO) | 87.1 | NaOH 25 mol % |

Example 2

Ether Carboxylic Acid Based on Oleyl Alcohol +5 EO

Oleyl alcohol was reacted analogously to Example 1 using 50 mol % of NaOH as catalyst, but, in contrast to Example 1, the residual alcohol content which remained was not distilled off.

The Table below shows the EO homolog distribution before the final alkylation step:

TABLE 2

|  | Standard ethoxylation | Example 2 |
|---|---|---|
| Catalyst | 1.0 mol % of NaOH | 50 mol % of NaOH |
| Degree of ethoxylation | 5.0 | 5.1 |
| Oleyl alcohol (area %) | 11.0 | 4.3 |
| Oleyl alcohol + 1 EO (area %) | 8.1 | 3.9 |
| Oleyl alcohol + 2 EO (area %) | 9.2 | 6.6 |
| Oleyl alcohol + 3 EO (area %) | 9.9 | 10.0 |
| Oleyl alcohol + 4 EO (area %) | 9.7 | 13.0 |
| Oleyl alcohol + 5 EO (area %) | 8.7 | 14.4 |
| Oleyl alcohol + 6 EO (area %) | 8.2 | 14.0 |
| Oleyl alcohol + 7 EO (area %) | 7.7 | 12.0 |
| Oleyl alcohol + 8 EO (area %) | 6.7 | 9.0 |
| Oleyl alcohol + 9 EO (area %) | 5.7 | 6.1 |
| Oleyl alcohol + 10 EO (area %) | 4.6 | 3.7 |
| Oleyl alcohol + 1 1 EO (area %) | 3.5 | 1.9 |
| Oleyl alcohol + 12 EO (area %) | 2.6 | 0.9 |
| Oleyl alcohol + 13 EO (area %) | 1.8 | 0.3 |
| Oleyl alcohol + 14 EO (area %) | 1.2 | 0.1 |

TABLE 2-continued

|  | Standard ethoxylation | Example 2 |
|---|---|---|
| Oleyl alcohol + 15 EO (area %) | 0.7 | — |
| Oleyl alcohol + 16 EO (area %) | 0.4 | — |
| Oleyl alcohol + 17 EO (area %) | 0.2 | — |
| Total area % | 100.0 | 100.0 |
| Oleyl alcohol (% by weight) | 9.3 | 4.6 |

Characteristics of the ether carboxylic acid:

|  | Acid number (mg KOH/g) | Content according to acid number (%) |
|---|---|---|
| Example 2 | 91.3 | 88.7 |
| Ether carboxylic acid based on standard ethoxylate | 83.4 | 79.3 |

What is claimed is:

1. A process for the preparation of ether carboxylic acids or alkali metal or ammonium salts thereof with low residual alcohol content, which comprises firstly converting a mono- or polyhydric alcohol into the corresponding alkoxide using a substoiciometric amount between 5 and 95 mol % of a basic compound selected from the group consisting of alkaline earth metal hydroxides, alkali metal hydroxides, and alkali metal alkoxides; then, reacting the alkoxide with alkylene oxides, and if necessary after distilling off the residual alcohol that remains, alkylating the highly alkaline reaction mixture, which comprises more than 5 mol % of alkoxylated alkoxides, directly with a chloroacetic acid derivative, and if necessary, converting the alkylated product into the free ether carboxylic acid by acidification with mineral acid.

2. The process as claimed in claim 1, where the mono- or polyhydric alcohol contains a total of from 1 to 30 carbon atoms.

3. The process as claimed in claim 2, where the alcohol is a $C_6$–$C_{22}$-fatty alcohol.

4. The process as claimed in claim 1, where the alkylene oxide is ethylene oxide, propylene oxide or butylene oxide.

5. The process as claimed in claim 1, where the amount of basic compound is between 15 and 90 mol %, based on the amount of mono- or polyhydric alcohol.

* * * * *